United States Patent [19]

Plymate

[11] 4,051,235
[45] Sept. 27, 1977

[54] METHOD OF PREPARING BOVINE COLOSTRUM FOR USE IN TREATING LIVESTOCK

[76] Inventor: Robert R. Plymate, 1079 South St., Blair, Nebr. 68008

[21] Appl. No.: 679,470

[22] Filed: Apr. 22, 1976

[51] Int. Cl.$^2$ ............................................ A61K 39/00
[52] U.S. Cl. ..................................................... 424/85
[58] Field of Search ........................... 424/85; 426/580

[56] References Cited
U.S. PATENT DOCUMENTS 3,646,193   2/1972   Michaelson ............................ 424/85

Primary Examiner—Sam Rosen
Attorney, Agent, or Firm—Zarley, McKee, Thomte, Voorhees & Sease

[57] ABSTRACT

The method of preparing bovine colostrum for use in treating livestock comprising the steps of:
1. Collecting bovine colostrum milk:
2. Removing substantially all of the fat from the colostrum milk:
3. Removing the casein from the colostrum milk to obtain bovine colosteral whey:
4. Dializing the whey:
5. Adjusting the pH of the dialsate to 4.0 to 4.5:
6. Precipitating the whey:
7. Removing the supernant from the precipitated whey:
8. Clarifying the supernant:
9. Adding a water, saline and phenol mixture to the clarified supernant to obtain the desired concentration:
10. Sterilizing the mixture; and
11. Placing the sterilized mixture into containers for subsequent storage and use.

9 Claims, No Drawings

METHOD OF PREPARING BOVINE COLOSTRUM FOR USE IN TREATING LIVESTOCK

BACKGROUND OF THE INVENTION

Milk contains one or more proteins of the globulin group although the amount present is usually quite small. The globulin group is generally considered to be comprised of lactoglobulin or beta lactoglobulin. The globulin of milk is very important. Under certain conditions it enables a mother to transmit immunity toward certain infections to her suckling. This takes place during the first 2 or 3 days of the young animal's life.

During the first few days of lactation, the secretion of the mammary gland differs a great deal from that of normal milk. The secretion is called colostrum. The first colostrum is very rich in globulin and fills the special needs of the newborn animal. Among these is a need for globulin, for the blood of the newborn of many species contains much less than the normal amount of this protein. Colostrum is an important source of antibodies for the newborn. The antibodies may either be the globulins themselves or are associated with the globulins. Colostrum is generally believed to be important in the case of the cow, goat, sheep, pig and mare.

DESCRIPTION OF THE PREFERRED METHOD

As previously stated, colostrum milk has been shown to be an important factor in the resistance of infectuous diseases in the young newborn which was nature's purpose for providing colostrum milk. The antibodies found in colostrum milk help the newborn fight diseases as well as protect them from future infection through immunal responses. It has also been found that a cow can be stimulated to produce certain antibodies to bacteria by injecting the cow before calving with antigens to the antibodies desired. Further, it has been found that a cow which has been subjected to many diseases during its lifetime will also have produced certain antibodies. When the cow calves, the first milk produced by the cow will contain antibodies to the stimulants as well as the normal environmental antibodies present in the mammory.

The colostrum milk is collected and the antibodies are removed therefrom and are manufactured into an injectible solution which may also be used orally to benefit other animals which may be subjected to the diseases which the particular antibodies are peculiar to.

Assuming that the cow has either been injected with certain antigens or that the cow simply has the normally occuring antibodies in the colostrum milk, the colostrum milk is collected after calving. Preferably, the colostrum milk is collected and frozen until a suitable quantity has been collected to enable the process to be carried out. The freezing of the colostrum milk also aids in subsequent removal of the fat from the colostrum milk. Examples I and II are two examples wherein the antibodies were recovered from the colostrum milk. Example I is the preferred process of recovering the antibodies while Example II is an alternate method for recovering the antibodies.

EXAMPLE I (PREFERRED)

The colostrum milk is collected and frozen. The milk is defatted by partially thawing the frozen milk and skimming the top liquid therefrom. The remaining milk is then completely thawed and centrifugally separated to remove as much of the remaining fat as possible.

The defatted colostrum milk is then precipitated by adding 1.5 mg of $CaCl_2$ per liter of milk and by adding one tablet (1.5 gram) of commercially available rennin per liter of milk. The mixture is then thoroughly stirred. The solution is then heated to 20°–80° C and again stirred. The solution is permitted to stand for 2–5 hours and the casein in the solution is then removed by filtration. The resultant solution is termed "bovine colosteral whey."

The whey is then dialized against tap water at 47° F with saline added for approximately 96 to 120 hours. The pH of the dialsate is adjusted to 4.0 to 4.5 with acetic acid. The whey is then precipitated by placing the same in vats having a controlled temperature of 35°–65° F. The supernant is siphoned off and centrifuged. The supernant is then clarified by filtration. The titre of the solution is determined in conventional fashion and a water, saline and 0.3% Phenol mixture is added to make a final bovine IGG concentration of 100 mg %.

The solution is then passed through a water sterilizer (ultraviolet) and placed in sterile 250 mg bottles and capped in ultraviolet light. The product is then ready for use.

EXAMPLE II

The colostrum milk is collected and centrifugally separated to remove as much of the fat as possible.

The defatted colostrum milk is then precipitated by adding 1.0–2.0 mg of $CaCl_2$ per liter of milk and by adding 0.5–1.5 tablets of commercially available rennin per liter of milk. The mixture is then thoroughly stirred. The solution is then heated to 20–80° C and again stirred. The solution is permitted to stand for 2–5 hours and the casein in the solution is then removed by filtration. The resultant solution is termed "bovine colosteral whey."

The whey is then dialized against tap water at 40°–54° F with saline added for approximately 96 to 120 hours. The pH of the dialsate is adjusted to 4.0 to 4.5 with acetic acid. The whey is then precipitated by placing the same in vats having a controlled temperature of 35°–65° F. The supernant is siphoned off and centrifuged. The supernant is then clarified by filtration. The titre of the solution is determined in conventional fashion and a water, saline and 0.3% Phenol mixture is added to make a final bovine IGG concentration of 100 mg %.

The solution is then passed through a water sterilizer (ultraviolet) and placed in sterile 250 mg bottles and capped in ultraviolet light. The product is then ready for use.

Thus it can be seen that the method of this invention accomplishes at least all of its stated objectives.

I claim:

1. The method of preparing bovine colostrum for use in treating livestock comprising the following steps,
    collecting bovine colostrum milk,
    removing substantially all of the fat from the colostrum milk,
    removing the casein from the colostrum milk to obtain bovine colosteral whey,
    dializing the whey,
    adjusting the pH of the dialsate to 4.0–4.5,
    precipitating the whey,
    removing the supernant from the precipitated whey,
    clarifying the supernant, adding a water, saline and phenol mixture to the clarified supernant to obtain the desired concentration, sterilizing the mixture, and placing the sterilized mixture into containers for subsequent storage and use.

2. The method of claim 1 wherein said bovine colostrum milk is frozen after collection, said frozen milk then being partially thawed, said fat being removed by skimming off the fat from the partially thawed milk.

3. The method of claim 2 wherein substantially all of the remaining fat is removed after the partially frozen milk is completely thawed.

4. The method of claim 3 wherein said fat is removed by centrifugal separation.

5. The method of claim 1 wherein the casein is removed by:
 a. adding approximately 1.0–2.0 mg of $CaCl_2$ per liter of milk;
 b. adding approximately 0.5–1.5 tablets of rennin per liter of milk;
 c. mixing the mixture;
 d. heating the mixture to 20–80° C;
 e. mixing the heated mixture;
 f. allowing the heated mixture to stand until the casein precipitates from the mixture; and
 g. filtrating the casein from the mixture.

6. The method of claim 5 wherein the whey is dialized against tap water having a temperature of 40°–54° F for approximately 96–120 hours.

7. The method of claim 6 wherein the whey is precipitated by heating the dialsate to 35°–65° F.

8. The method of claim 7 wherein the supernant of the precipitated whey is removed from the mixture and centrifuged.

9. The method of claim 8 wherein water, saline and 0.3% Phenol mixture is added to make a final bovine IGG concentration of 100 mg %.

* * * * *